United States Patent
Porter

(10) Patent No.: US 6,953,473 B2
(45) Date of Patent: Oct. 11, 2005

(54) DETACHABLE DEVICE WITH ELECTRICALLY RESPONSIVE ELEMENT

(75) Inventor: Stephen Christopher Porter, Fremont, CA (US)

(73) Assignee: Boston Scientific SciMed, Inc., Maple Grove, MN (US)

(*) Notice: Subject to any disclaimer, the term of this patent is extended or adjusted under 35 U.S.C. 154(b) by 380 days.

(21) Appl. No.: 10/029,568

(22) Filed: Dec. 20, 2001

(65) Prior Publication Data

US 2003/0120300 A1 Jun. 26, 2003

(51) Int. Cl.⁷ .............................................. A61B 17/00
(52) U.S. Cl. ........................ 606/213; 606/200; 606/191; 606/194; 606/198
(58) Field of Search ............................... 606/200, 213, 606/191, 194, 195, 198; 604/49–63; 623/1.11–1.21

(56) References Cited

U.S. PATENT DOCUMENTS

| | | |
|---|---|---|
| 5,122,136 A | 6/1992 | Guglielmi et al. |
| 5,354,295 A | 10/1994 | Guglielmi et al. |
| 5,423,829 A | 6/1995 | Pham et al. |
| 5,540,680 A | 7/1996 | Guglielmi et al. |
| 5,643,254 A | 7/1997 | Scheldrup et al. |
| 5,669,905 A | 9/1997 | Scheldrup et al. |
| 5,749,894 A | * 5/1998 | Engelson ..................... 606/213 |
| 5,851,206 A | 12/1998 | Guglielmi et al. |
| 5,925,037 A | 7/1999 | Guglielmi et al. |
| 5,944,714 A | 8/1999 | Guglielmi et al. |
| 5,964,797 A | * 10/1999 | Ho ............................. 606/194 |
| 6,296,622 B1 | 10/2001 | Kurz et al. |
| 6,478,773 B1 | * 11/2002 | Gandhi et al. .............. 604/113 |
| 6,648,911 B1 | * 11/2003 | Sirhan et al. .............. 623/1.15 |

FOREIGN PATENT DOCUMENTS

| | | |
|---|---|---|
| EP | 0 707 830 A1 | 10/1995 |
| EP | 0 941 703 A1 | 9/1999 |
| WO | WO 98/37816 | 9/1998 |
| WO | WO 99/09895 | 3/1999 |
| WO | WO 01/58366 A1 | 8/2001 |

* cited by examiner

Primary Examiner—Vy Bui
(74) Attorney, Agent, or Firm—Bingham McCutchen LLP

(57) ABSTRACT

An endovascular device assembly includes a delivery member to deliver the assembly endoluminally to an aneurysm, a detachable endovascular device including a thermo-resistive element to deliver heat to the device by passing a first electrical current through the thermo-resistive element, whereupon the device expands to a predetermined shape. The endovascular device is connected to the delivery member by a detachable joint, such as an electrolytic sacrificial joint that separates by passing a second electrical current therethrough, to deploy the device within the aneurysm to promote embolization.

14 Claims, 6 Drawing Sheets

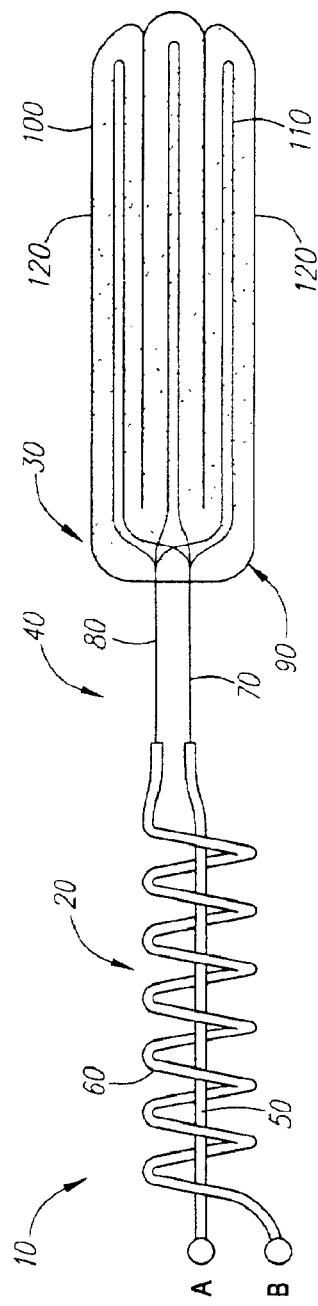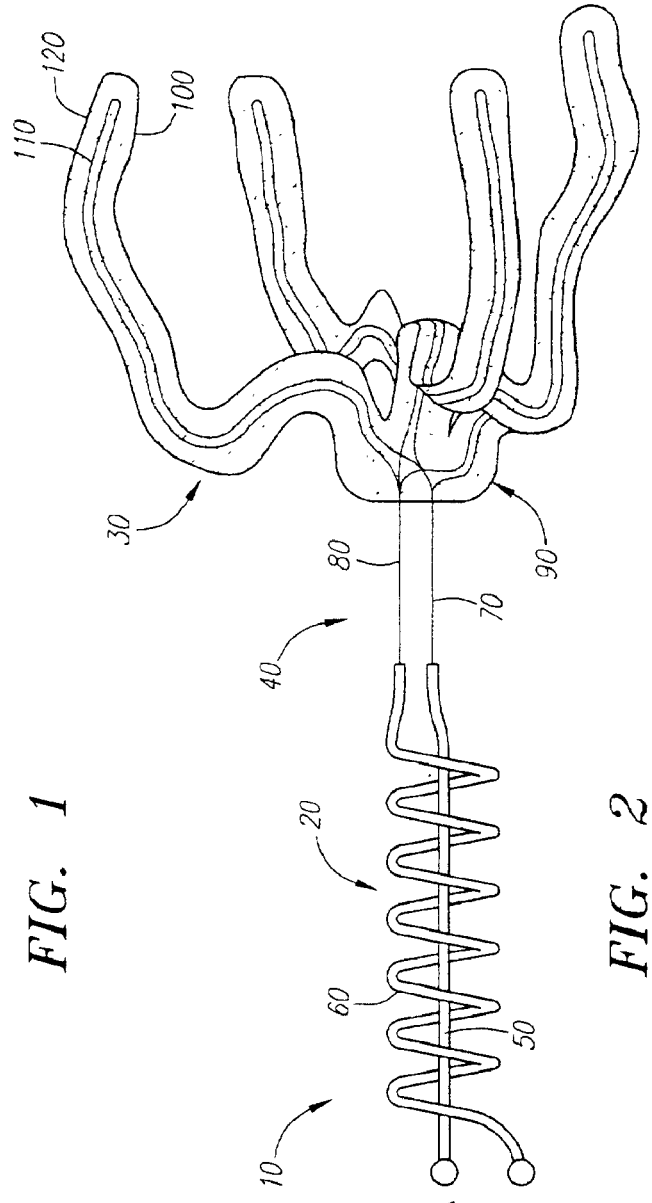

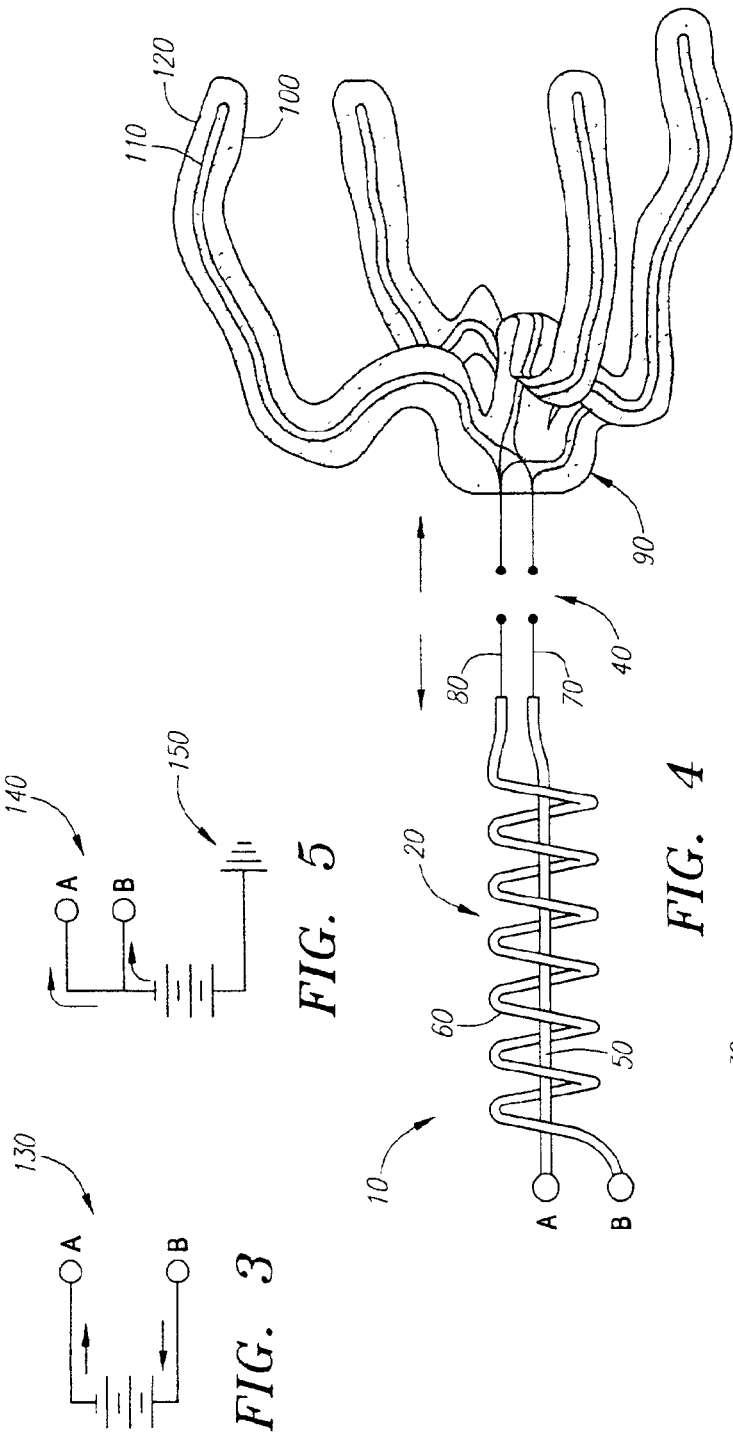

DETACHABLE DEVICE WITH ELECTRICALLY RESPONSIVE ELEMENT

FIELD OF THE INVENTION

The invention relates generally to a detachable device including an electrically responsive element, and, in particular, to an electrolytically or mechanically detachable endovascular device including a thermo-resistive element.

BACKGROUND

Like all parts of the body, the brain is composed of living cells that require a blood supply to provide oxygen and nutrients. A hemorrhage in a blood vessel in the brain or in the space closely surrounding the brain is a common cause of strokes. Hemorrhage refers to bleeding into the brain, usually because of a problem with a blood vessel, for example, an aneurysm.

An aneurysm is an abnormal bulging and/or weakening of a blood vessel wall. The wall may smoothly bulge outwardly in all directions (a fusiform aneurysm) or it may form a sack arising from one wall (a saccular aneurysm). If the aneurysm ruptures, a hemorrhage occurs. This can compress and irritate the surrounding blood vessels, resulting in a reduced supply of oxygen and nutrients to the cells, possibly causing a stroke.

Aneurysms can be treated from outside the blood vessel using surgical techniques or from inside the blood vessel using endovascular techniques. Endovascular treatment of an aneurysm is performed using a catheter. X-ray, magnetic resonance imaging (MRI) equipment, or other visualization equipment may be used to view the progress during a procedure.

Electrolytically detachable embolic devices have been proposed to fill aneurysms. A core wire or catheter may be used to introduce an embolic coil into an aneurysm. The embolic coil may be attached to the distal end of the core wire by an electrolytic sacrificial joint. Once the embolic coil is located in the targeted aneurysm, the coil may be detached from the core wire and deployed in the aneurysm by running an electric current through the electrolytic sacrificial joint. Within a short period of time after the filling the aneurysm with the embolic coil, a thrombus may form in the aneurysm and, shortly thereafter, complemented with a collagenous material that significantly lessens the potential of the aneurysm rupturing.

The inventor of the present invention has recognized that embolic devices may utilize shape-memory polymers or metals, polymer-coated coils fused together by heat, or other thermo-sensitive materials for thermally controlled expansion of the embolic devices in aneurysms. Warm saline injections may be used to deliver localized heat to these devices, but this method of heat delivery may be difficult to reproduce in a controllable manner. Further impediments to this concept may include differential mixing of saline with blood due to dissimilar thermodynamics, non-uniform heat distribution, heat transfer out of the catheter, and/or physician compliance in maintaining reasonable saline temperature and injection rates.

SUMMARY OF THE INVENTION

One aspect of the invention involves a detachable thermo-sensitive embolic device that utilizes thermo-resistive heating to cause more uniform heating of the embolic device and more consistent performance than using warm saline to control heating of an embolic device. This aspect allows electrical heating of the detachable thermo-sensitive embolic device to expand the device in an aneurysm for embolization. In addition, the embolic device is connected to a delivery device by a detachable joint, thereby enabling the embolic device to be deployed within a target treatment region within a patient, e.g., within an aneurysm. In one embodiment, the detachable joint may be an electrolytically erodible joint, allowing electrical heating to electrolytically detach the device to deploy the device into the aneurysm. In other embodiments, the detachable joint may include one or more mechanical connectors to detachably connect the embolic device to the delivery device.

On a broader level, another aspect of the invention involves a detachable device including an electrically responsive element. The device may receive a first current to activate the electrically responsive element. If the device includes an electrolytically erodible joint, a second current may be used to electrolytically detach and deploy the device. Alternatively, other detachable joints may be used. Embodiments of the electrically responsive element include, but are not limited to, a thermo-resistive element, an expandable thermo-resistive element, a MEMS (microelectromechanical system) micro actuator, an electrically stimulated contractile element, a light emitting diode, a piezoelectric crystal, an electromagnetic element, and a sensor.

Another aspect of the present invention involves a detachable endovascular device assembly for embolizing an aneurysm. The assembly includes a delivery member to deliver the assembly to the aneurysm for embolization, a detachable endovascular device including a thermo-resistive element to deliver heat to the device with passage of a first electrical current through the thermo-resistive element and the device adapted to take a predetermined shape as a result of the heating, and a detachable joint for separating the device from the delivery member. In one embodiment, the joint may be an electrolytic sacrificial joint joining the device and the delivery member that may separate when a second electrical current is delivered therethrough to deploy the device into the aneurysm for embolization. Alternatively, the joint may be a mechanical or interference fit joint that may be released by mechanically moving one element of the joint or by applying a force to the joint, e.g., using fluid pressure.

An additional aspect of the present invention involves a method for embolizing an aneurysm with a detachable endovascular device assembly. The method includes delivering a detachable endovascular device assembly to a targeted aneurysm, the detachable endovascular device assembly including a delivery member and a detachable endovascular device joined by a releasable joint. The detachable endovascular device may include a thermo-resistive element to heat the detachable endovascular device to cause the detachable endovascular device to take a predetermined shape as a result of heating from the thermo-resistive element. The detachable endovascular device may be introduced into the aneurysm, and expanded within the aneurysm by supplying a first current to the thermo-resistive element. This causes the thermo-resistive element to heat the detachable endovascular device so that the detachable endovascular device expands to a predetermined shape in the aneurysm.

The detachable endovascular device may then be deployed or released into the aneurysm and the delivery member removed. In one embodiment, a second current may be supplied to a electrolytic sacrificial joint, causing the electrolytic sacrificial joint to separate and the detachable endovascular device to detach from the detachable endovascular device assembly and be deployed into the aneurysm for embolization. Alternatively, the detachable endovascular device may be deployed by releasing cooperating connectors, or by using fluid pressure or other force to overcome an interference fit between a portion of the detachable endovascular device, or using an induction current transfer.

A further aspect of the invention involves a detachable device assembly that includes a delivery member to deliver the assembly to a target location, an electrolytically detachable device including an electrically responsive element activatable with passage of a first electrical current through the electrically responsive element, and a releasable joint joining the detachable device and the delivery member.

A still further aspect of the invention involves a method of using a detachable device assembly that includes delivering the detachable device assembly to a target location, the detachable device assembly including a delivery member, a detachable device including an electrically responsive element activatable with passage of a first electrical current through the electrically responsive element, and a releasable joint joining the detachable device and the delivery member. Once the assembly is at the target location, the electrically activatable element of the detachable device may be activated by supplying a first current to the electrically activatable element, and the detachable device may be deployed at the target location. In one embodiment, the detachable device includes an electrolytic sacrificial joint such that the detachable device may be deployed at the target location by supplying a second current to the electrolytic sacrificial joint, causing the electrolytic sacrificial joint to separate and the detachable device to detach from the detachable device assembly. Alternatively, the detachable device may be released using force to overcome an interference fit or by releasing one or more mechanical connectors.

Other features and advantages of the invention will be evident from reading the following detailed description, which is intended to illustrate, but not limit, the invention.

BRIEF DESCRIPTION OF THE DRAWINGS

The drawings illustrate the design and utility of preferred embodiments of the present invention, in which similar elements are referred to by common reference numerals.

FIG. 1 is a side view of an endovascular device assembly including a detachable endovascular device in a collapsed position, before the device is electroresistively heated and expanded.

FIG. 2 is a side view of the endovascular device assembly of FIG. 1, with the electrolytically detachable endovascular device in an expanded position after the device is electroresistively heated and expanded.

FIG. 3. is a circuit diagram for supplying electrical current to an electrolytically detachable endovascular device assembly to electro-resistively heat and expand the device.

FIG. 4 is a side view of the endovascular device assembly of FIG. 1, with the electrolytically detachable endovascular device separating from the rest of the assembly.

FIG. 5. is a circuit diagram for supplying electrical current to an electrolytic sacrificial joint for electrolytically detaching an endovascular device.

FIG. 6 is a side view of one embodiment of the detachable device of FIGS. 1, 2, and 4 illustrating the relationship of the resistance Rd of the device and the resistance Rm of the medium or electrolytic path between conductors of an electrolytic sacrificial joint.

DETAILED DESCRIPTION OF THE PREFERRED EMBODIMENTS

Figure 7A:
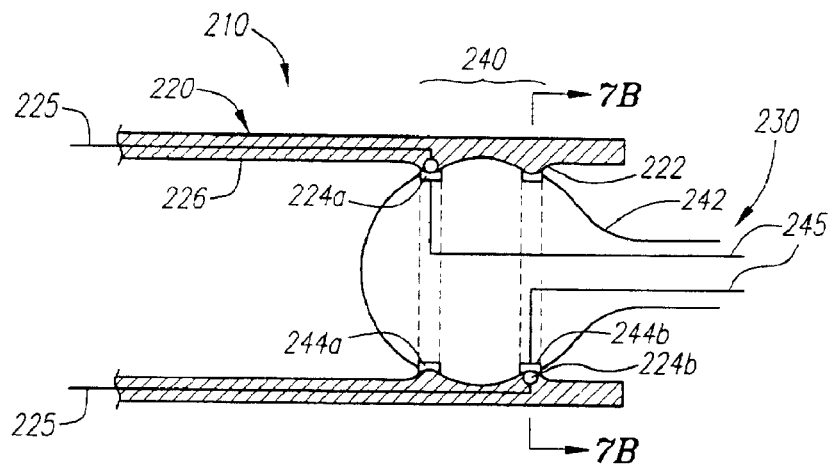
FIG. 7A is a cross-sectional side view showing a first embodiment of an interference fit joint for releasably joining a detachable device to a delivery member.

With reference to FIG. 1, an endovascular device assembly 10 is shown that includes a delivery member 20 and a detachable, thermo-resistive, expandable, embolic device 30. In the embodiment shown, the embolic device 30 is joined to the delivery member 20 by an electrolytic sacrificial joint 40. The device assembly 10 may be used for embolizing an aneurysm, although the device assembly 10 may also be adaptable for treating other conditions, such as endovascular occlusions in arteries, veins, vascular malformations, and arteriovenous fistulas. The device assembly 10 may also be used for forming an occlusion in other areas of a mammalian body, or for other purposes or applications. For example, the device assembly 10 may include one or more detachable, electrically responsive elements other than the detachable, thermo-resistive, expandable, embolic device 30 such as a microelectromechanical system (MEMS), an electrically stimulated contractile element, a light emitting diode, a piezoelectric crystal, an electromagnetic element, or a sensor.

In the embodiment shown, the delivery member 20 includes an insulated, conductive pusher wire 50 helically wrapped with an insulated, conductive return wire 60. In another embodiment, the delivery member 20 may include a catheter (not shown) with delivery and return wires carried by the catheter. For example, a delivery wire may be located along a longitudinal axis of the catheter and a return wire may be located in an outer sheath of the catheter.

The electrolytic sacrificial joint 40 is preferably similar to the electrolytic sacrificial joint of the Guglielmi Detachable Coil (GDC) manufactured by Boston Scientific/Target of Fremont, Calif. Further, the assembly 10 could be powered by current generated from a standard Guglielmi Detachable Coil (GDC) power supply made by Boston Scientific/Target using a simple reusable electronic plug-in coupling.

The electrolytic sacrificial joint 40 includes a bare conductive portion or detachment wire 70 of the push wire 50 and a bare conductive portion or detachment wire 80 of the return wire 60. The detachment wires 70, 80 form the sacrificial joint or corrosion junctions 40.

The detachable, thermo-resistive, expandable, embolic device 30 may include an insulated hub 90 where the electrolytic sacrificial joint 40 joins the detachable device 30. The detachable device 30 may include multiple appendages 100 extending from the hub 90. Each appendage 100 may include a platinum-tungsten (PtW) alloy wire or thin film loop 110. However, the wire or thin film loops 110 may be made of other materials, such as silver, silver-chloride, copper, platinum, chromium, aluminum, titanium, and nickel either in their pure form or as a combination thereof. Thin films can be applied to the device 30 by, for example, adhering cut sheet constructs of the films to the device 30, or by selectively masking the device 30 and vapor-depositing or sputter coating the conducting material onto the device 30. Preferably, the wire or thin film loops 110 are also radio-opaque to allow for radiographic visualization.

A first end of each wire loop 110 may be attached to the push wire 70 and a second, opposite end of each wire loop 110 may be attached to the return wire 80. The wire loops 110 form thermo-resistive heating elements that heat up with the passage of electrical current therethrough. The wire loops 110 may be encased in a thermo-sensitive, shape memory polymer 120 that expands (FIG. 2) when heated by the wire loops 110. Preferably, the detachable device 30 expands to a shape having a larger diameter or other cross-section than that before application of current/heat. Other thermo-sensitive materials may be used to cause the device 30 to expand when heated by electrical current. For example, polymer-coated, pre-shaped memory coils may be fused together, and, upon application of heat, the polymer becomes flowable, allowing the pre-shaped memory coils to take their natural expanded shape.

Although four electrically responsive thermo-resistive elements 110 are shown, the detachable embolic device 30 may include other numbers of elements 110 (e.g., 1, 2, 3, 5, 6, etc.).

In use, the endovascular device assembly 10 is delivered to a target aneurysm site via the delivery member 20, by insertion through the lumen of a micro-catheter, the distal end of the micro-catheter having been previously positioned at the aneurysm site. Once at the aneurysm site, the detachable, thermo-resistive, expandable, embolic device 30 may be introduced into the aneurysm. The detachable embolic device 30 may be electrically actuated and thermally expanded by supplying a first current through the thermo-resistive coils 110 of the detachable embolic device 30. The first current passes through the push wire 50 and the exposed conductive wire 70, through the thermo-resistive coils 110, and returns through the exposed conductive wire 80 and the return wire 60. Electrical current through the thermo-resistive wire loops 110 causes the loops 110 and, hence, the thermo-sensitive shape memory polymer to be heated. The thermo-sensitive shape memory polymer expands into a configuration, such as that shown in FIG. 2, causing it to be retained within the aneurysm. Although the detachable embolic device 30 is shown as having a hand-like configuration, the detachable embolic device 30 may have any expanded configuration.

FIG. 3 illustrates a simple electrical diagram of a power supply circuit 130 for supplying a first current to the assembly 10 in the manner described above. Points A, B of the circuit 130 may correspond to or otherwise may be coupled to points A, B of the assembly 10. The direction of DC current is shown in the electrical diagram of FIG. 3. In another embodiment, the first current may be AC current.

With reference to FIG. 6, the first current passes through the electrolytic sacrificial joint 40 without causing the joint 40 to separate because an overall resistance Rd of the thermo-resistive elements 110 (not shown in FIG. 6 for simplicity) of the device 30 is less than a resistance Rm of the electrolytic path or medium (e.g., blood) between the exposed, conductive wires 70, 80. Some current leakage from the wires 70, 80 may result in some corrosion of the wires 70, 80, but current leakage may be controlled by designing or adjusting the resistivity Rd of the device 30. Using AC current for the first current helps to inhibit accidental corrosion of the wires 70, 80.

With reference to FIGS. 4 and 5, once the localized heating and expansion of the detachable device 30 in the aneurysm has been accomplished, a second current in the same direction is supplied to the wires 50, 60 by a circuit 140 such as that shown in FIG. 5. The second current returns to a ground or return electrode 150 on or in the patient. A bias between the two wires 70, 80 and the ground 150 causes the electrolytically sacrificial joint to corrode and separate, as shown in FIG. 4. The second current is maintained until the device 30 has detached from the rest of the assembly 10. Within a short period of time after filling the aneurysm with the embolic device 30, a thrombus forms in the aneurysm and is shortly thereafter complemented with thrombus and eventually, a collagenous material, which significantly lessens the potential for aneurysm rupture.

In summary, by utilizing thermo-resistive heating, compared to warm saline heating, the detachable thermo-sensitive embolic device assembly 10 may cause more uniform heating of the embolic device 30 and more consistent performance. The assembly 10 also overcomes other problems associated with saline heating, such as differential mixing of saline with blood due to dissimilar thermodynamics, non-uniform heat distribution, heat transfer out of the catheter, and physician compliance in maintaining reasonable saline temperature and injection rates.

As indicated above, on a broader level, the detachable device assembly may include an electrolytically detachable device with one or more electrically responsive elements other than or in addition to a thermo-electric element(s). Examples of other types of electrically responsive elements that may be used include microelectromechanical systems electrically stimulated contractile elements, light emitting diodes, piezoelectric crystals, electromagnetic elements, or sensors.

In addition, other detachable joints may be provided for any of the embodiments described herein, instead of the electrolytic sacrificial joint 40 described above. For example, turning to FIGS. 7A–7D, an interference fit joint 240 may be provided that may simultaneously mechanically secure and electrically couple an embolic device or other electrically responsive element 230 to a delivery member 220 to provide a unitary assembly 210.

Figure 7B:
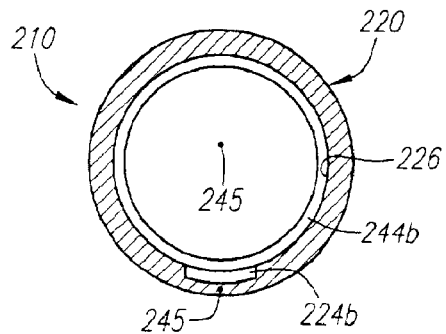
FIG. 7B is a cross-section of the interference fit joint of FIG. 7A, taken along line 7B—7B.

With particular reference to FIGS. 7A and 7B, the interference fit joint 240 may include a bulbous member or other connector 242 that extends from the electrically responsive element 230, for example, from the hub 90 of the embolic device 30 (not shown, see FIG. 2). The connector 242 includes contacts or other electrically conductive regions 244a, 244b thereon, e.g., extending around the bulbous member 242 and spaced apart axially from one another that are coupled to respective leads 245. The leads 245 may be coupled to an electrically responsive element (not shown), such as those described above. The delivery member 220, e.g., a catheter or other tubular member, includes mating connectors 222 including contacts or other electrically conductive regions 224a, 224b thereon and a lumen or other recess 226 defined by the connectors 222. Leads 225 may extend from the contacts 224, e.g., proximally within a wall of the delivery member 220, to a source of electrical energy (not shown).

In one embodiment, the connectors 222 on the delivery member 220 may be annular ribs that extend inwardly into the lumen 222 with the contacts 224a, 224b thereon. The bulbous member 242 may be a fluid-filled or solid body biased to expand to a size large than the lumen 222, yet sufficiently flexible to allow insertion into the lumen 222. The ribs 222 may grip or otherwise engage the bulbous member 242 when it is received in the lumen 226, thereby securing the bulbous member 242, and, consequently, the electrically responsive element 230 to the delivery member 220. In addition, when the bulbous member 242 is fully seated in the lumen 226, the contacts 224, 244 may be coupled to one another, thereby electrically coupling the leads 225, 245 to one another, and, consequently, the electrically responsive element 230 to the source of electrical energy.

Figure 8A:
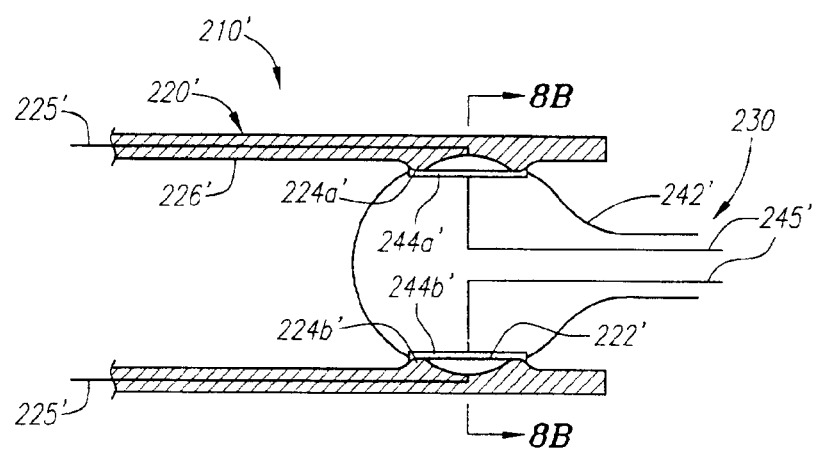
FIG. 8A is a cross-sectional side view showing a second embodiment of an interference fit joint for releasably joining a detachable device to a delivery member.
Figure 8B:
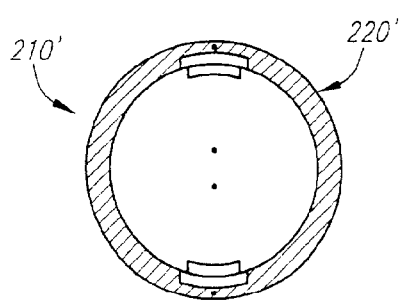
FIG. 8B is a cross-section of the interference fit joint of FIG. 8A, taken along line 8B—8B.

In an alternative embodiment, shown in FIGS. 8A and 8B, the connectors 222' may be longitudinal gripping elements that are spaced apart about the circumference of the lumen 226, e.g., disposed opposite one another. In this alternative, contacts 244a', 244b' may be provided on the bulbous member 242' that may cooperate with the contacts 224' on the delivery member 220,' e.g., may be disposed opposite one another and extend axially along the bulbous member 242.' Thus, when the bulbous member 242' is engaged within the lumen 226,' the leads 225', 245' may be coupled to one another, similar to the previous embodiment.

Figure 7C:
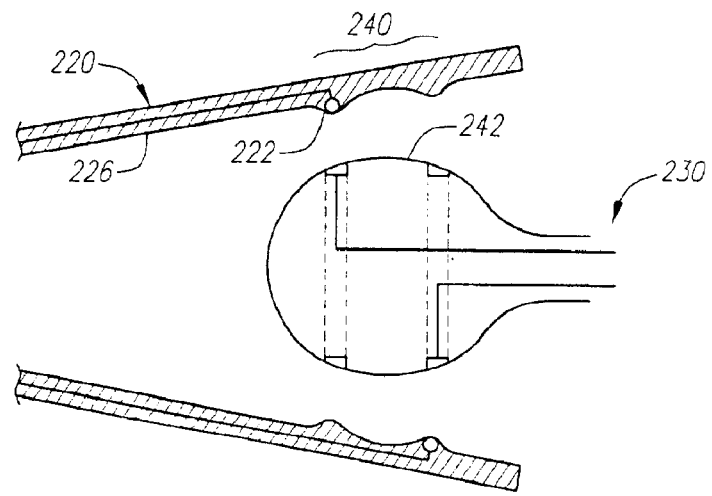
FIG. 7C is a cross-sectional side view of the interference fit joint of FIG. 7A, including an expandable connector for releasing the detachable device.
Figure 7D:
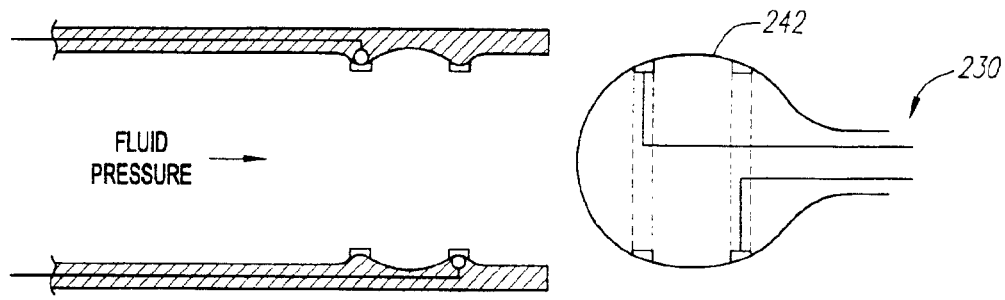
FIG. 7D is a cross-sectional side view of the interference fit joint of FIG. 7A, showing use of fluid pressure to release the detachable device.

Turning to FIGS. 7C and 7D, the connector(s) 222 on the delivery member 220 may be disengaged from the bulbous member 242 to release the electrically responsive element 230 from the delivery member 220. For example, the delivery member 220 may be expandable to direct the connectors 222 away from one another, thereby increasing the size of the lumen 226, as shown in FIG. 7C. Alternatively, the connectors 222 may be gripping elements (not shown) that may be mechanically actuated from a proximal end (not shown) of the delivery member 220 to release the electrically responsive element 230. In a further alternative, the bulbous member 242 may be compressible inwardly to release the electrically responsive element 230 (not shown). In yet a further alternative, shown in FIG. 7D, the bulbous member 242 may be resiliently compressible such that it may be forced into the lumen 226 and held frictionally between the connectors 222. To deploy the electrically responsive element 230, a fluid or pusher member (not shown) may be introduced into the lumen 226 with sufficient pressure to overcome the interference fit and push the bulbous member 242 out of the lumen 226.

Figure 9A:
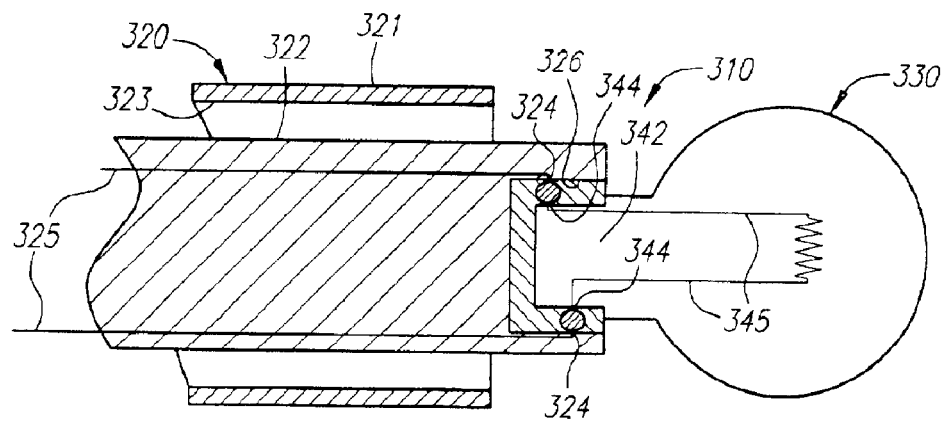
FIGS. 9A–9C are cross-sectional side views showing alternative embodiments of detachable joints for releasably joining a detachable device to a delivery member.

Turning to FIG. 9A, another embodiment of an assembly 310 is shown that includes a delivery device 320 and a detachable device 330, e.g., an electrically responsive device, as described above. The delivery device 320 generally includes a catheter or other tubular member 321 and a pusher member 322 slidably disposed within a lumen 323 of the catheter 321. The pusher member 322 includes a recess 326 within a distal end thereof for receiving a hub or other connector 342 extending from the detachable device 330. Leads 325, 345 in the catheter 321 and the pusher member 322 may be coupled to one another by cooperating contacts 324, 344 when the hub 342 is fully received within the recess 326.

The hub 342 may be secured within the recess 326 by an interference fit, an electrolytic sacrificial joint, mechanical connector(s), and the like, similar to the embodiments described above. For example, the contacts 324, 344 may include a relatively thin conductive wire connecting them that may be eroded upon application of a predetermined electrical current. Alternatively, the hub 342 may be slidably received within the recess 326, e.g., by friction, yet deployable by pushing the hub 342 out of the recess 326, e.g., using an internal or external pusher element (not shown) that may be advanced distally relative to the pusher member 322 against the hub 342.

During use, the detachable device 330 may be disposed within the lumen 323 of the catheter 321, and the catheter 321 may be advanced, e.g., endoluminally within a patient's vasculature, to a target site, e.g., an aneurysm within a cranial artery or other blood vessel (not shown). Alternatively, the catheter 321 may be advanced to the target site, e.g., over a guidewire (not shown), and then the pusher member 322 with the detachable device 330 thereon may be delivered through the lumen 323 of the catheter 321. The pusher member 322 may be advanced distally to expose the detachable device 330. Electrical energy from a power source (not shown) may be delivered to the detachable device 330, via the leads 325, 345, e.g., to heat and/or expand the detachable device 330, similar to the embodiments described above. The detachable device 330 may then be deployed, i.e., released, from the pusher member 322, whereupon the catheter 312 and pusher member 322 may be withdrawn, leaving the detachable device 330 at the target site.

Figure 9B:
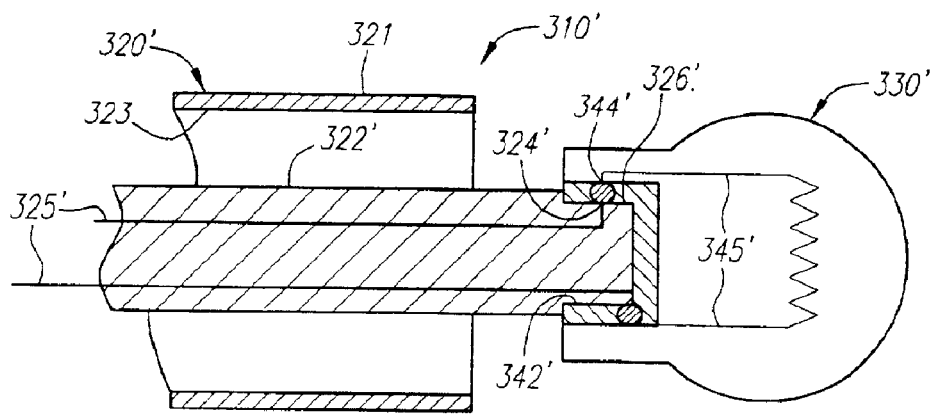

Alternatively, as shown in FIG. 9B, a pusher member 322' may include a hub 326' and a detachable device 330' may include a recess 342.' Leads 325,' 345' and contacts 324,' 344' may be provided, similar to the previous embodiment. The detachable device 330' may be releasably secured to the pusher member 322' and/or may be deployed similar to the previous embodiment.

Figure 9C:
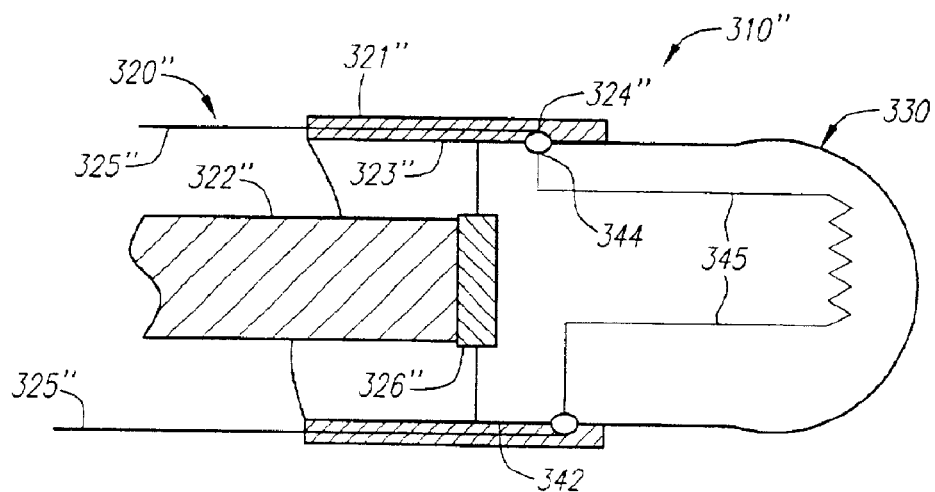

Turning to FIG. 9C, yet another alternative embodiment of an assembly 310" is shown that includes a delivery device 320," including a catheter 321" and a pusher member 322" slidably disposed within a lumen 323" of the catheter 321, and a detachable device 330, similar to the previous embodiments. Unlike the previous embodiment, the catheter 321" includes contacts 324" and leads 325," which may be coupled to an electrical power source (not shown). A hub 342" of the detachable device 330 may be received in the lumen 323" such that contacts 344 on the hub 342" contact the contacts 324" on the catheter 321," thereby coupling the detachable device 330 to the power source. The pusher member 322" may include a distal end 326" that may abut the hub 342 such that, upon advancement of the pusher member 322," the hub 342 may be pushed out of the lumen 323" to deploy the detachable device 330. Alternatively, the distal end 326" of the pusher member 322" and/or the hub 342 may include one or more connectors (not shown) for releasably connecting the detachable device 330 to the pusher member 322."

Figure 10A:
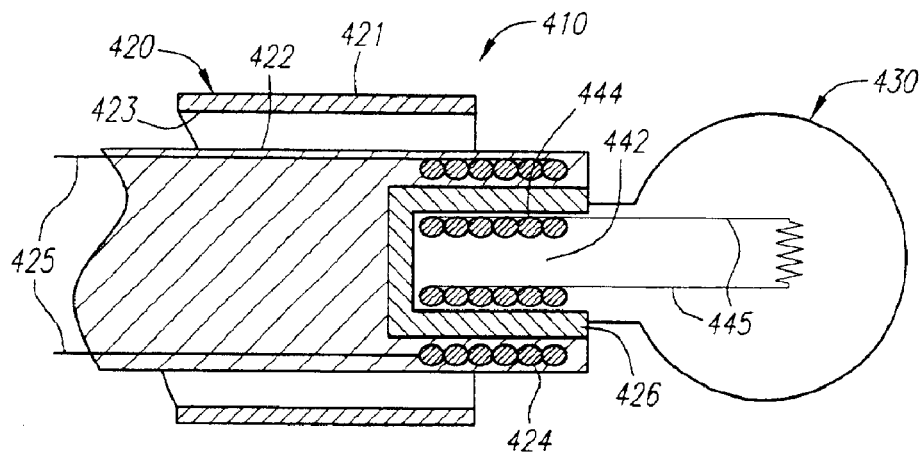
FIGS. 10A–10C are cross-sectional side views showing detachable joints including induction current transfer elements for transferring electrical energy form a delivery device to a detachable device.
Figure 10B:
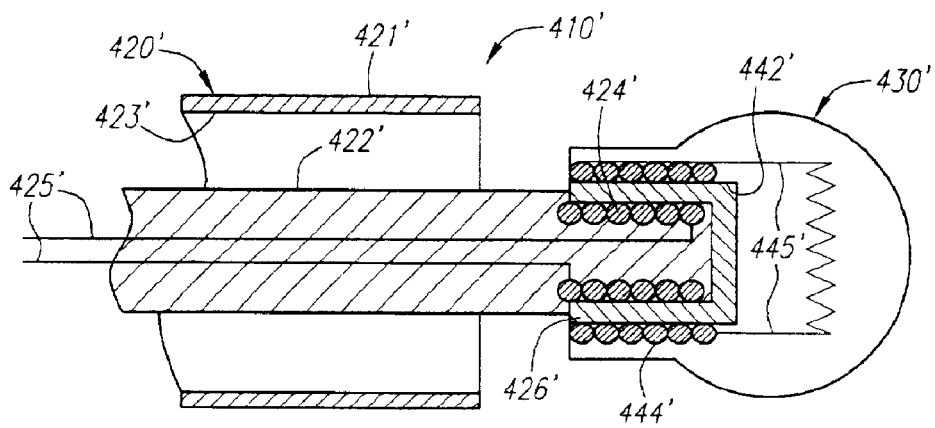
Figure 10C:
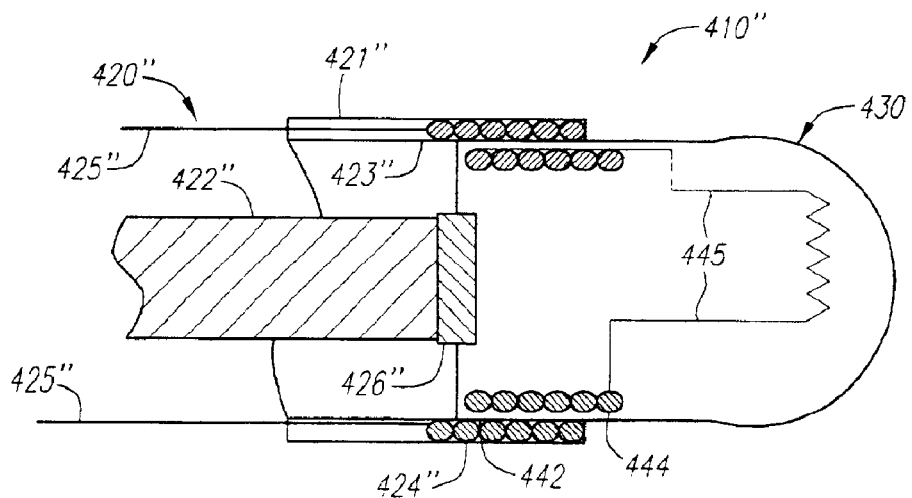

Turning to FIGS. 10A–10C, embodiments of detachable joints are shown that use induction current transfer to transfer electrical energy to an electrically responsive element, rather than physical contacts, as described above. For example, as shown in FIG. 10A, an assembly 410 is shown that includes a delivery device 420, including a catheter 421 and a pusher member 422, and a detachable device 430. The pusher member 422 may include a recess 426 for receiving a hub 442 extending from the detachable device 430, similar to the previous embodiments. In addition, the pusher member 422 includes a coil 424 coupled to leads 425, and the hub 442 includes a coil 444 coupled to leads 445. The coil 424 on the pusher member 422 may surround the recess 426 such that the coil 424 may be inductively coupled to the coil 444 when the hub 442 is received in the recess 426. Thus, electrical energy, e.g., from an RF generator (not shown) coupled to the leads 425, may be delivered to the detachable device 430 via the concentric coils 424, 444, as is known to those skilled in the art.

The hub 442 may be secured within the recess 426 by an interference fit and/or cooperating connectors (not shown), similar to the previous embodiments, that allow the detachable device 430 to be deployed from the delivery device 420. For example, the hub 442 may be secured within the recess 426 by an interference fit and/or one or more mechanical connectors. Alternatively, as shown in FIG. 10B, the pusher member 422' may include a hub 426' that may be received within a recess 442 within the detachable device 430.' In yet a further alternative, shown in FIG. 10C, the catheter 420" may include a coil 424" that may surround the coil 444 when the hub 442 is received in a lumen 423" of the catheter 421" to inductively couple the leads 425," 445 to one another. The pusher member 422" and/or the hub 442 may include cooperating connectors (not shown), e.g., on a distal end 426" of the pusher member 422" for detachably securing the detachable device 430 to the pusher member 422," similar to the embodiments described above. Delivery and/or deployment of the detachable device 430 may proceed similar to the previous embodiments, except that a direct electrical connection is not necessary. Thus, precise alignment of the hub 442 within the recess 426 may not be required, as may be required for cooperating contacts, while still allowing delivery of electrical energy to the detachable device 430 before its deployment from the delivery device 420, as will be appreciated by those skilled in the art.

While embodiments and applications of this invention have been shown and described, it would be apparent to those in the field that many more modifications are possible without departing from the inventive concepts herein. The invention, therefore, is not to be restricted except in the spirit of the appended claims.

What is claimed is:

1. A detachable endovascular device assembly, comprising:
   a delivery member to deliver the detachable endovascular device assembly to an aneurysm in a body;
   a detachable endovascular device including a thermo-resistive element to deliver heat to the detachable endovascular device with passage of a first electrical current through the thermo-resistive element and the detachable endovascular device adapted to take a predetermined shape as a result of the heating; and
   a detachable joint joining the detachable endovascular device to the delivery member and adapted to separate to deploy the detachable endovascular device into the aneurysm for embolization thereof, and the detachable joint comprises an electrolytic sacrificial joint joining the detachable endovascular device and the delivery member and adapted to separate with passage of a second electrical current therethrough to deploy the detachable endovascular device into the aneurysm for embolization thereof.

2. The assembly of claim 1, wherein the electrolytic sacrificial joint includes a first conductive wire and a second conductive wire with an electrolytic path therebetween having an electrical resistance, and the thermo-resistive element of the detachable endovascular device having an electrical resistance lower than the electrical resistance of the electrolytic path.

3. The assembly of claim 1, wherein the delivery member includes a catheter.

4. The assembly of claim 1, wherein the delivery member includes a push wire.

5. The assembly of claim 1, wherein the detachable endovascular device includes a thermo-sensitive, shape memory material that takes a predetermined shape when heated by the thermo-resistive element.

6. The assembly of claim 1, wherein the detachable endovascular device includes a thermo-resistive, shape memory element and a polymer that normally holds the detachable endovascular device in a compact configuration and deforms upon heating of the polymer with the thermo-resistive, shape memory element, causing the detachable endovascular device to take a predetermined shape dictated by the thermo-resistive, shape memory element.

7. The assembly of claim 1, wherein the thermo-resistive element may be one or more thermo-resistive elements.

8. The assembly of claim 1, wherein the thermo-resistive element is made of a platinum-tungsten (PtW) alloy.

9. The assembly of claim 1, wherein the thermo-resistive element includes a thermo-resistive wire.

10. The assembly of claim 1, wherein the thermo-resistive element includes a thin film.

11. The assembly of claim 1, wherein the thermo-resistive element is radio-opaque.

12. A detachable device assembly for treating a patient, comprising:
    a delivery member to deliver an electrolytically detachable device assembly to a target location within a patient, the detachable device including an electrically responsive element activatable by passing a first electrical current through the electrically responsive element; and
    a detachable joint joining the detachable device to the delivery member and adapted to separate to deploy the detachable device from the delivery member, the detachable joint comprises an electrolytic sacrificial joint joining the detachable device and the delivery member and adapted to separate by passing a second electrical current therethrough to deploy the detachable device at the target location.

13. The assembly of claim 12, wherein the electrically responsive element includes a thermo-resistive element to deliver heat to the detachable device with passage of the first electrical current through the thermo-resistive element and the detachable device adapted to take a predetermined shape as a result of the heating.

14. The assembly of claim 12, wherein the electrically responsive element comprises one or more electrically activatable elements.

* * * * *